(12) United States Patent
Roselli et al.

(10) Patent No.: US 10,335,272 B2
(45) Date of Patent: Jul. 2, 2019

(54) APPARATUS AND METHOD FOR REPAIRING THE FUNCTION OF A DISEASED VALVE

(71) Applicant: THE CLEVELAND CLINIC FOUNDATION, Cleveland, OH (US)

(72) Inventors: Eric E. Roselli, Rocky River, OH (US); Douglas R. Johnston, Shaker Hts., OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 66 days.

(21) Appl. No.: 15/372,602

(22) Filed: Dec. 8, 2016

(65) Prior Publication Data

US 2017/0165059 A1    Jun. 15, 2017

Related U.S. Application Data

(60) Provisional application No. 62/266,889, filed on Dec. 14, 2015.

(51) Int. Cl.
*A61F 2/24* (2006.01)
*A61F 2/06* (2013.01)
(Continued)

(52) U.S. Cl.
CPC .......... *A61F 2/2418* (2013.01); *A61F 2/2409* (2013.01); *A61F 2/2415* (2013.01);
(Continued)

(58) Field of Classification Search
CPC ................................. A61F 2/24; A61F 2/2418
(Continued)

(56) References Cited

U.S. PATENT DOCUMENTS

| 7,799,072 B2 | 9/2010 | Greenburg |
| 8,979,924 B2 | 3/2015 | Greenberg |

(Continued)

FOREIGN PATENT DOCUMENTS

| EP | 2929860 | 10/2015 |
| WO | WO 2003/003949 | 1/2003 |
| WO | WO 2016/089777 | 6/2016 |

OTHER PUBLICATIONS

International Search Report Corresponding to U.S. Patent No. PCT/US2016/065525, 14 pages, dated Apr. 3, 2017.

*Primary Examiner* — Suzette J Gherbi
(74) *Attorney, Agent, or Firm* — Tarolli, Sundheim, Covell & Tummino LLP (57) ABSTRACT

An apparatus for repairing the function of a diseased valve includes a tubular first support member which is expandable to a first average diameter and has oppositely disposed proximal and distal first support member ends. A tubular second support member is spaced axially apart from the first support member and is expandable to a second average diameter that is smaller than the first average diameter. The second support member has oppositely disposed proximal and distal second support member ends. A tubular graft section interconnects the first and second support members and has oppositely disposed proximal and distal graft section ends axially spaced apart by a graft section body. The proximal graft section end is connected directly to the distal first support member end and the distal graft section end is connected directly to the proximal second support member end.

12 Claims, 4 Drawing Sheets

(51) Int. Cl.
*A61F 2/07* (2013.01)
*A61F 2/848* (2013.01)
*A61F 2/915* (2013.01)

(52) U.S. Cl.
CPC ... *A61F 2002/061* (2013.01); *A61F 2002/075* (2013.01); *A61F 2002/8483* (2013.01); *A61F 2002/91525* (2013.01); *A61F 2250/006* (2013.01); *A61F 2250/0039* (2013.01); *A61F 2250/0063* (2013.01); *A61F 2250/0064* (2013.01); *A61F 2250/0067* (2013.01); *A61F 2250/0097* (2013.01); *A61F 2250/0098* (2013.01)

(58) Field of Classification Search
USPC .................................................. 623/2.14–2.19
See application file for complete search history.

(56) References Cited

U.S. PATENT DOCUMENTS

| | | |
|---|---|---|
| 9,566,149 B2 | 2/2017 | Shaw |
| 2004/0093070 A1 | 5/2004 | Hojeibane et al. |
| 2004/0106976 A1 | 6/2004 | Bailey et al. |
| 2006/0276813 A1* | 12/2006 | Greenberg ............ A61F 2/2418 606/158 |
| 2013/0144373 A1* | 6/2013 | Shahriari ................... A61F 2/07 623/1.12 |
| 2014/0316513 A1* | 10/2014 | Tang ..................... A61F 2/2412 623/1.16 |
| 2015/0025625 A1* | 1/2015 | Rylski ................... A61F 2/2412 623/2.14 |
| 2016/0081829 A1* | 3/2016 | Rowe .................... A61F 2/2412 623/1.12 |
| 2016/0151153 A1* | 6/2016 | Sandstrom ............ A61F 2/2418 623/2.18 |
| 2016/0158007 A1* | 6/2016 | Centola ................. A61F 2/2439 623/1.26 |
| 2016/0235525 A1* | 8/2016 | Rothstein .............. A61F 2/2418 |
| 2016/0262880 A1* | 9/2016 | Li ........................ A61F 2/2418 |
| 2018/0147047 A1* | 5/2018 | Bradway ................. A61F 2/07 |

* cited by examiner

APPARATUS AND METHOD FOR REPAIRING THE FUNCTION OF A DISEASED VALVE

RELATED APPLICATION

This application claims priority from U.S. Provisional Application Ser. No. 62/266,889, filed 14 Dec. 2015, the subject matter of which is incorporated herein by reference in its entirety.

TECHNICAL FIELD

This disclosure related to an apparatus and methods for repairing the function of a diseased valve, such as a cardiac or venous valve, via an endovascular technique, and is further directed to methods for providing the apparatus.

BACKGROUND

It is known to implant prosthetic valves in various body passages to replace native valves that are diseased or otherwise defective in some manner. Blood pressure, as provided by heart activity via the arteries, is normally sufficient to maintain the flow of blood in one direction through the vasculature. The blood pressure in the veins is much lower than in the arteries and venous valves function to limit the backflow of blood through the veins. Numerous such venous valves are located throughout the venous system and are particularly important to maintaining directional blood flow in the lower extremities.

Venous valves can become incompetent and lead to chronic venous insufficiency. Various surgical techniques have been developed for treating incompetent venous valves including valvuloplasty, transplantation, and replacement with a prosthetic valve. These known surgical techniques include both open and percutaneous approaches. As with any prosthetic, compatibility issues for prosthetic venous valves are important, along with the need to avoid thrombosis and platelet deposition.

Another common type of prosthetic valve is a prosthetic cardiac valve. Prosthetic cardiac valves have been used to replace all four of the native cardiac valves. Cardiac valve replacement has traditionally been done though an invasive open surgical procedure, although endovascular (or percutaneous) approaches are being developed.

The four native cardiac valves (mitral, aortic, tricuspid, and pulmonary) serve to direct the flow of blood through the two sides of the heart in a forward direction. On the left (systemic) side of the heart, the mitral valve is located between the left atrium and the left ventricle, while the aortic valve is located between the left ventricle and the aorta. These two valves direct oxygenated blood coming from the lungs, through the left side of the heart, into the aorta for distribution to the body. On the right (pulmonary) side of the heart, the tricuspid valve is located between the right atrium and the right ventricle, while the pulmonary valve is located between the right ventricle and the pulmonary artery. These two valves direct de-oxygenated blood coming from the body, through the right side of the heart, into the pulmonary artery for distribution to the lungs, where it again becomes re-oxygenated to begin the circuit anew.

All four of these native cardiac valves are passive structures that do not themselves expend any energy and do not perform any active contractile function. The valves consist of moveable leaflets that open and close in response to differential pressures on either side of the valve. The mitral and tricuspid valves are referred to as atrioventricular valves because they are situated between an atrium and a ventricle on each side of the heart. The mitral valve has two leaflets and the tricuspid valve has three leaflets. The aortic and pulmonary valves are referred to as semilunar valves because of the unique appearance of their leaflets, which are often termed "cusps" and which are shaped somewhat like a half-moon. The aortic and pulmonary valves each have three cusps.

Cardiac valves can exhibit abnormal anatomy and function as a result of congenital or acquired valve disease. Congenital valve abnormalities may be so severe that emergency surgery is required within the first few hours of life, or they may be well-tolerated for many years only to develop a life-threatening problem in an elderly patient. Acquired valve disease may result from causes such as rheumatic fever, degenerative disorders of the valve tissue, bacterial or fungal infections, and trauma.

The two major problems that can develop with cardiac valves are stenosis, in which a valve does not open properly, and insufficiency (also called regurgitation), in which a valve does not close properly. Stenosis and insufficiency may occur concomitantly in the same valve or in different valves. Both of these abnormalities increase the workload and stress placed on the heart. The severity of this increased stress on the heart, and the heart's ability to adapt to it, determine whether the abnormal valve will have to be surgically repaired or replaced.

In addition to stenosis and insufficiency of cardiac valves, surgery may also be required for certain types of bacterial or fungal infections in which the valve may continue to function normally, but nevertheless harbors an overgrowth of bacteria on the leaflets of the valve that may flake off (or embolize) and lodge downstream in a vital artery. If this occurs on the valves of the left side (i.e., the systemic circulation side) of the heart, embolization results in sudden loss of the blood supply to the affected body organ and immediate malfunction of that organ. The organ most commonly affected by such embolization is the brain, in which case the patient suffers a stroke. Thus, surgical replacement of either the mitral or the aortic valve may be necessary for this problem even though neither stenosis nor insufficiency of either valve is present.

If a cardiac valve must be replaced, there are currently several options available, and the choice of a particular type of prosthesis (i.e., artificial valve) depends on factors such as the location of the valve, the age and other specifics of the patient, and the surgeon's experiences and preferences. Available prostheses include mechanical valves, tissue valves, and homograft valves.

Mechanical valves include caged-ball valves, bi-leaflet valves, and tilting disk valves. The main advantage of mechanical valves is their long-term durability. Their main disadvantage is that they require the patient to take systemic anticoagulation drugs for the rest of his or her life, because of the propensity of mechanical valves to cause blood clots to form on them.

Tissue valves are typically constructed either by sewing the leaflets of porcine aortic valves to a stent (to hold the leaflets in proper position), or by constructing valve leaflets from porcine or bovine pericardial tissue and sewing them to a stent. The stents may be rigid or slightly flexible and are typically covered with a fabric, such as the material sold under the trademark DACRON™, and then attached to a sewing ring for fixation to the patient's native valve annulus. The porcine or bovine tissue is chemically treated to alleviate any antigenicity (i.e., to reduce the risk that the patient's body will reject the foreign tissue). Tissue valves may be used to replace any of the heart's four valves. The main advantage of tissue valves is that they do not cause blood clots to form as readily as do the mechanical valves, and therefore, they do not necessarily require systemic anticoagulation.

Homograft valves are harvested from human cadavers. Homograft valves are most commonly implanted in the aortic position, but are also occasionally implanted in the pulmonary position. Homograft valves are specially prepared and frozen in liquid nitrogen, where they are stored for later use. The advantage of aortic homograft valves is that they appear to be as durable as mechanical valves, but do not promote blood clot formation and therefore do not require anticoagulation. The main disadvantage of these valves is that they are not available in sufficient numbers to satisfy the needs of patients who need new aortic or pulmonary valves. Homograft valves are also extremely expensive and can be more difficult to implant than either mechanical valves or tissue valves.

Cardiac valve replacement using any of the aforementioned prostheses has traditionally been done via an open surgical technique in which the thoracic cavity is opened. This exacting operation requires use of a heart-lung machine for external circulation of the blood as the heart is stopped and opened during the surgical intervention and the artificial cardiac valve is implanted under direct vision. This operation exposes the patient to many risks especially in the elderly population. Hence, an apparatus for repairing the function of a diseased cardiac or venous valve via an endovascular (or percutaneous) procedure, rather than an open surgical procedure, could offer tremendous benefits for these patients, many of whom have no options today.

SUMMARY

In an aspect, an apparatus for repairing the function of a diseased valve is described. A tubular first support member is expandable to a first average diameter and has oppositely disposed proximal and distal first support member ends. A tubular second support member is spaced axially apart from the first support member and is expandable to a second average diameter that is smaller than the first average diameter. The second support member has oppositely disposed proximal and distal second support member ends. A tubular graft section interconnects the first and second support members and defines an annulus axially spaced from both the first and second support members. The tubular graft section has oppositely disposed proximal and distal graft section ends axially spaced apart by a graft section body. The proximal graft section end is connected directly to the distal first support member end and the distal graft section end is connected directly to the proximal second support member end. A diameter of the tubular graft section at the proximal graft section end is larger than a diameter of the tubular graft section at the distal graft section end.

In an aspect, a method for making an apparatus to repair the function of a diseased valve is described. A tubular first support member expandable to a first average diameter and having oppositely disposed proximal and distal first support member ends is provided. A tubular second support member spaced axially apart from the first support member and expandable to a second average diameter that is smaller than the first average diameter is provided. The second support member has oppositely disposed proximal and distal second support member ends. A tubular graft section having oppositely disposed proximal and distal graft section ends axially spaced apart by a graft section body is provided. A diameter of the tubular graft section at the proximal graft section end is larger than a diameter of the tubular graft section at the distal graft section end. The first and second support members are interconnected with the graft section. An annulus axially spaced from both the first and second support members is defined with the graft section. The proximal graft section end is connected directly to the distal first support member end. The distal graft section end is connected directly to the proximal second support member end.

BRIEF DESCRIPTION OF THE DRAWINGS

For a better understanding, reference may be made to the accompanying drawings, in which.

DESCRIPTION OF ASPECTS OF THE DISCLOSURE

Unless defined otherwise, all technical and scientific terms used herein have the same meaning as is commonly understood by one of skill in the art to which the present disclosure pertains.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, farm animals, livestock, etc.

As used herein, the terms "treat" or "treating" can refer to therapeutically regulating, preventing, improving, alleviating the symptoms of and/or reducing the effects of a diseased valve. As such, treatment also includes situations where a diseased valve, or at least a symptom associated therewith, is completely inhibited, e.g., prevented from happening or stopped (e.g., terminated) such that the subject no longer suffers from the diseased valve, or at least the symptom(s) associated therewith.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature may not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

The invention comprises, consists of, or consists essentially of the following features, in any combination.

Figure 1:
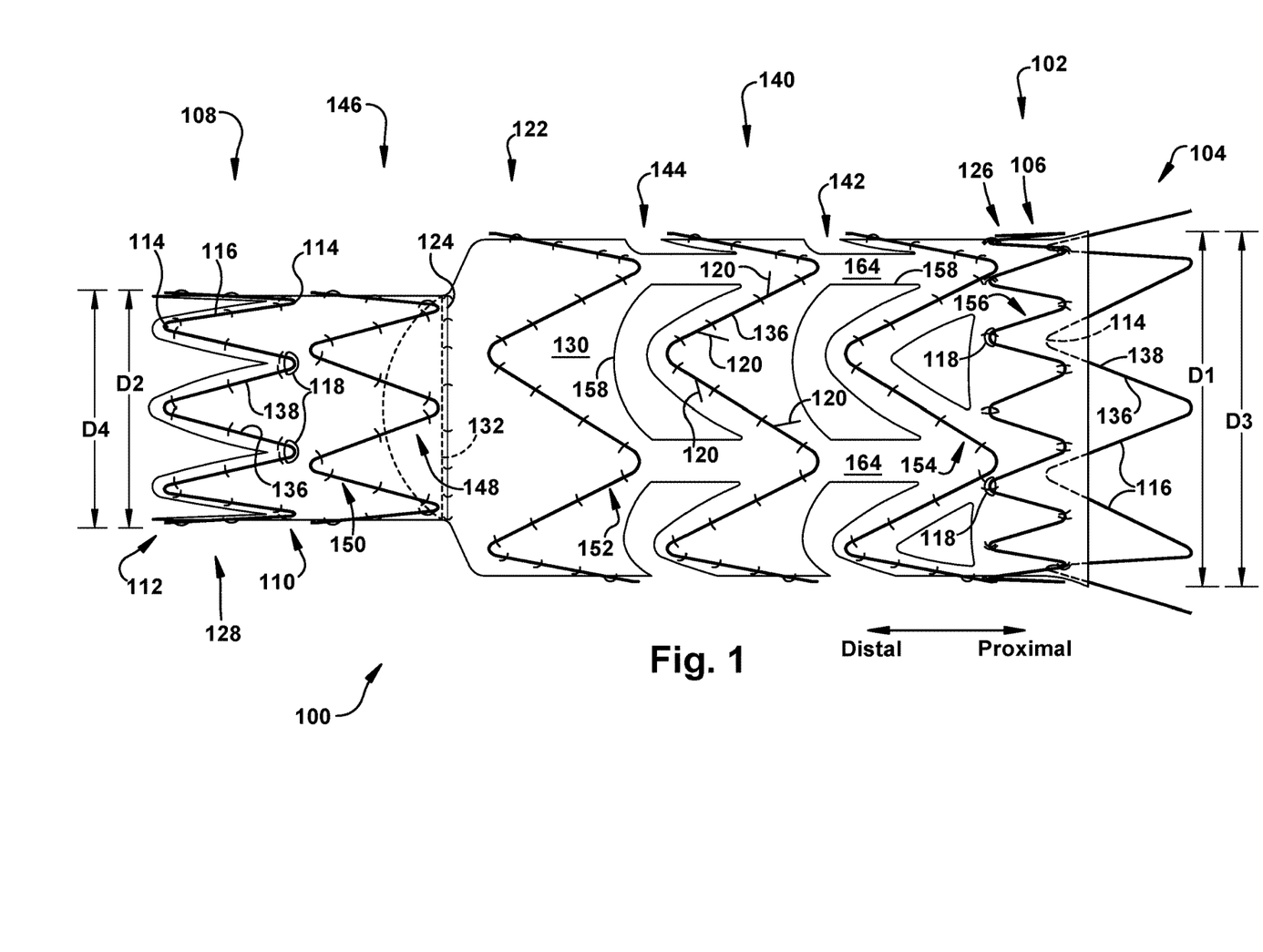
FIG. 1 is a side view of an aspect of the present invention.
Figure 4:
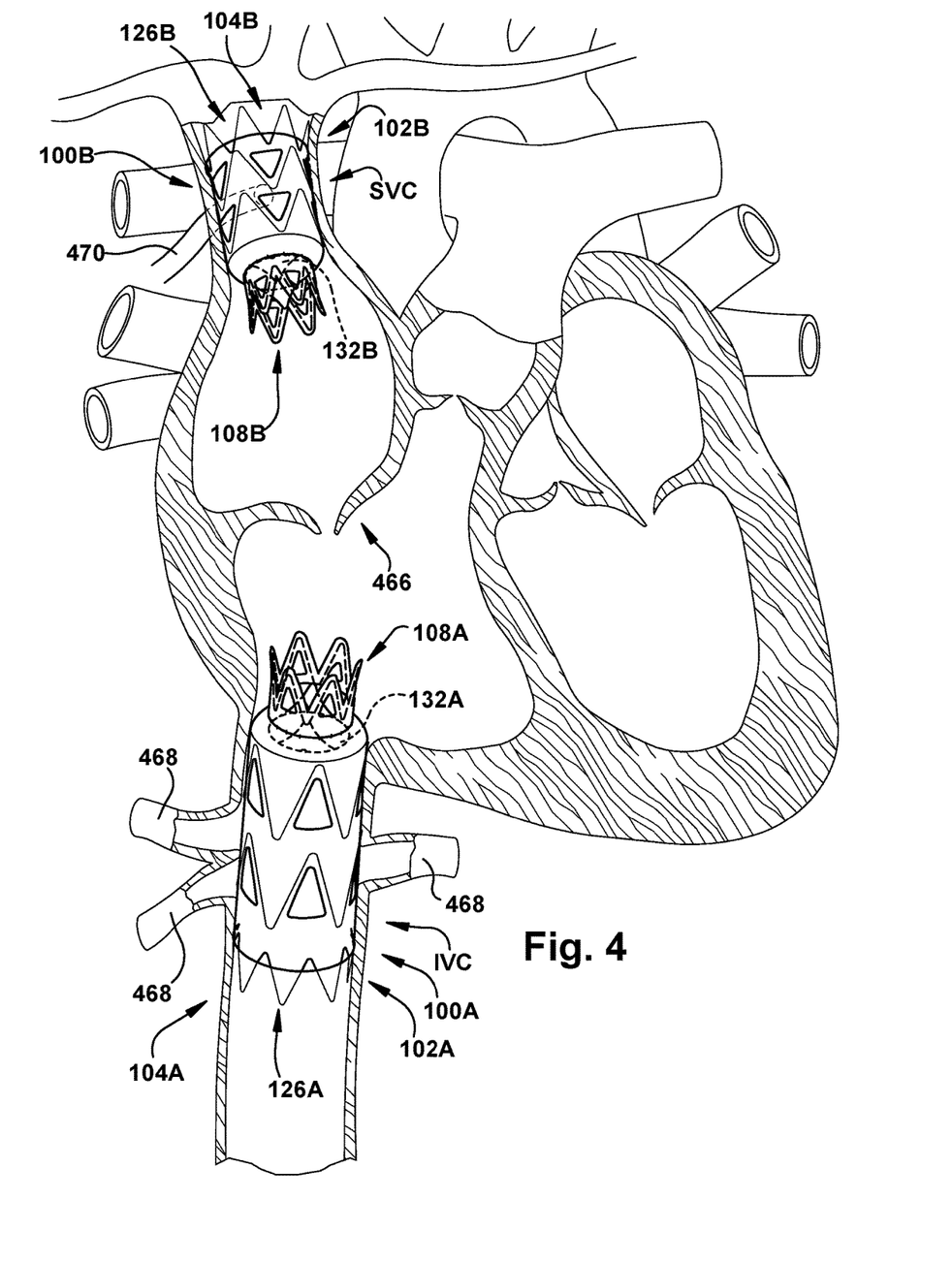
FIG. 4 is a schematic view of the aspect of FIGS. 1-3 in an example use environment.

FIG. 1 schematically depicts an apparatus 100 for repairing the function of a diseased valve, such as a tricuspid valve shown schematically in FIG. 4. It should be apparent, however, to those skilled in the art that the apparatus 100 disclosed herein can also be used to repair the function of other cardiac valves as well as venous valves.

The apparatus 100 includes a tubular first support member 102 expandable to a first average diameter D1 and having oppositely disposed proximal and distal first support member ends 104 and 106, respectively. A tubular second support member 108 is spaced axially apart from the first support member 102 and is expandable to a second average diameter D2 that is smaller than the first average diameter D1. The second support member 108 has oppositely disposed proximal and distal second support member ends 110 and 112, respectively.

The term "average diameter" is used herein to indicate a diameter that is an average of a plurality of diameters taken at substantially equidistant spacing along the length of the support member. The "average" diameter is not necessarily the diameter of the support member at a selected proximal or distal end thereof. The first and second support members 102 and 108 have their corresponding proximal and distal support member ends, each comprising a plurality of apices 114 connected by substantially longitudinally extending beams 116, to provide the first and second support members 102 and 108 with a known "M" or "Z" shape.

The first and second support members 102 and 108 are shown and described herein as each comprising a self-expanding stent made from shape memory metals such as Nitinol, but could alternatively be any suitable self-expanding or balloon-expandable stent, and could be made from any suitable medical grade plastic or metal, including stainless steel and Nitinol.

Any desired structure of the first and/or second support members 102 and 108 could include a plurality of eyelets 118 spaced as desired. The first and/or second support members 102 and 108 may further include a plurality of hooks (or barbs) 120 located in any desired location, such as on the outer surface of the beams 116, as shown. The hooks 120, when present, may extend radially outward and at an angle to prevent migration of the support member 102 or 108 upon implantation. It should be understood that the location, quantity, configuration, and orientation of the hooks 120 and eyelets 118 may be altered depending on specific needs of the apparatus 100.

It should also be understood that that the invention is not limited to the particular configuration of the illustrated first and second support members 102 and 108, and that the first and second support members 102 and 108 need not be configured similarly to each other. Further, it is contemplated that the longitudinal (i.e., proximal-to-distal) lengths of the first and second support members 102 and 108 will be varied based on the needs of a particular implantation. In addition, it should be noted that radiopaque markers (not shown) may be attached at various locations on the first and second support members 102 and 108 to aid with placement of the apparatus 100 under fluoroscopy.

To enhance the biocompatibility of the apparatus 100, it is contemplated that at least a portion of the first and second support members 102 and 108, or of any other structure(s) of the apparatus 100, may be provided with a therapeutic agent such as, but not limited to, an anti-coagulant, an anti-thrombogenic agent, an anti-proliferative agent, an anti-inflammatory agent, an antibiotic, an angiogenesis agent, a statin, a growth factor, or stem cells. The therapeutic agent may be, for example, loaded into a compound or polymer that is coated onto the first and second support members 102 and 108, or any other structure(s) of the apparatus 100, for a time-delayed release into surrounding tissue. Additionally or alternatively, structures of the first and second support members 102 and 108 (or of any other structure[s] of the apparatus 100) may be impregnated with a therapeutic agent, as desired.

A tubular graft section 122 interconnects the first and second support members 102 and 108 and defining an annulus 124 axially spaced from both the first and second support members 102 and 108. The tubular graft section 122 has oppositely disposed proximal and distal graft section ends 126 and 128, respectively, axially spaced apart by a graft section body 130. The proximal graft section end 126 is connected directly to the distal first support member end 106 and the distal graft section end 128 is connected directly to the proximal second support member end 110. A diameter of the tubular graft section 122 at the proximal graft section end 126 is larger than a diameter of the tubular graft section 122 at the distal graft section end 128.

The graft section 122 may comprises a biocompatible material such as Dacron®, woven velour, polyurethane, PTFE, heparin-coated fabric, or the like. Alternatively or additionally, the graft section 122 may include a biological material such as bovine or equine pericardium, a homograft, an autograft, or cell-seeded tissue.

A prosthetic valve (shown schematically at 132) may be secured within the annulus 124 of the graft section 122. The prosthetic valve 132 has at least two valve leaflets (shown schematically at 134) that are coaptable to permit the unidirectional flow of blood. Whether or not the prosthetic valve 132 is present, the first and second support members 102 and 108 may be interconnected only by the graft section 122. When present, the prosthetic valve 132 may be directly secured only to the graft section 122. The prosthetic valve 132 may be a homograft, an autograft, and/or made from a harvested biological material including, but not limited to, bovine pericardial tissue, equine pericardial tissue or porcine pericardial tissue. Alternatively or additionally, the prosthetic valve 132 may be made from a biocompatible synthetic material including, but not limited to, polyurethane and expanded PTFE. The prosthetic valve may also be part of a collapsible stented apparatus that is delivered in a staged fashion into the device 100 at the level of the annulus 124 at the base of segment 108.

Optionally, the graft section 122 may underlie and be secured to an inner surface (shown schematically at 136) of at least one of the first and second support members 102 and 108. Also optionally, the graft section 122 may overlap and be secured to an outer surface (shown schematically at 138) of one of the first and second support members 102 and 108. Finally, the graft section 122 may also or instead overlap and be secured to an outer surface 138 of one of the first and second support members 102 and 108, whether or not the graft section 122 underlies and is secured to the inner surface 136 of the other of the first and second support members 102 and 108.

A tubular third support member 140 may be spaced axially apart from, and distal to, the first support member 102 and be expandable to a third average diameter D3 that is substantially similar to the first average diameter D1, as shown in the Figures. When present, the third support member 140 may have oppositely disposed proximal and distal third support member ends 142 and 144, respectively. The third support member 140 is connected directly to the graft section body 130. The graft section 130 may underlie and be secured to an inner surface 136 of the third support member 140.

A tubular fourth support member 146 may be spaced axially apart from, and proximal to, the second support member 108 and be expandable to a fourth average diameter D4 that is substantially similar to the second average diameter D2. When present, the fourth support member 146 may have oppositely disposed proximal and distal fourth support member ends 148 and 150, respectively. The fourth support member 146 is connected directly to the graft section body 130. The graft section 130 may underlie and be secured to an inner surface 136 of the fourth support member 146.

It is contemplated that any desired number of support members may be provided as desired, and one of ordinary skill in the art will be able to extrapolate the described relationships to accommodate additional support members having any desired placements, configurations, and other physical properties relative to the support members described in detail above. For example, and as shown in the Figures, fifth, sixth, and seventh support members 152, 154, and 156, respectively (each being similar to the third support member 140) may be provided.

Regardless of the number and type of support members provided, however, the graft section body 130 may include at least one graft aperture 158 penetrating therethrough. The graft aperture(s) 158 may be provided in any position, and for any reason, whether or not related to the reason that the apparatus 100 is provided. For example, one or more graft apertures 158 may be provided to allow for access to nearby blood vessels (e.g., the hepatic veins) and to accommodate branch vessels. Graft apertures 158 may also be provided to reduce the amount of total apparatus 100 material that needs to be loaded into the delivery catheter (e.g., reducing the packing density of material loaded into the catheter).

The graft aperture(s) 158, when present, may be located axially (i.e., longitudinally) between circumferentially corresponding portions of axially adjacent ones (e.g., between longitudinally adjacent pairs) of the first, second, third, and/or fourth support members 102, 108, 140, and 146, or of any other support members provided, such as, but not limited to, the fifth, sixth, and seventh support members 152, 154, and 156. For example, and as shown in FIG. 1, a plurality of graft apertures are provided in the graft section body 130 longitudinally between the first and sixth support members 102 and 154, and a plurality of graft apertures are provided in the graft section body 130 longitudinally between the third and fifth support members 140 and 152. As another example, shown in FIGS. 2-3, a plurality of graft apertures 158 are provided in the graft section body 130 longitudinally between the first and third support members 102 and 140, and a plurality of graft apertures 158 are provided in the graft section body 130 longitudinally between the second and fourth support members 108 and 146.

Figure 2:
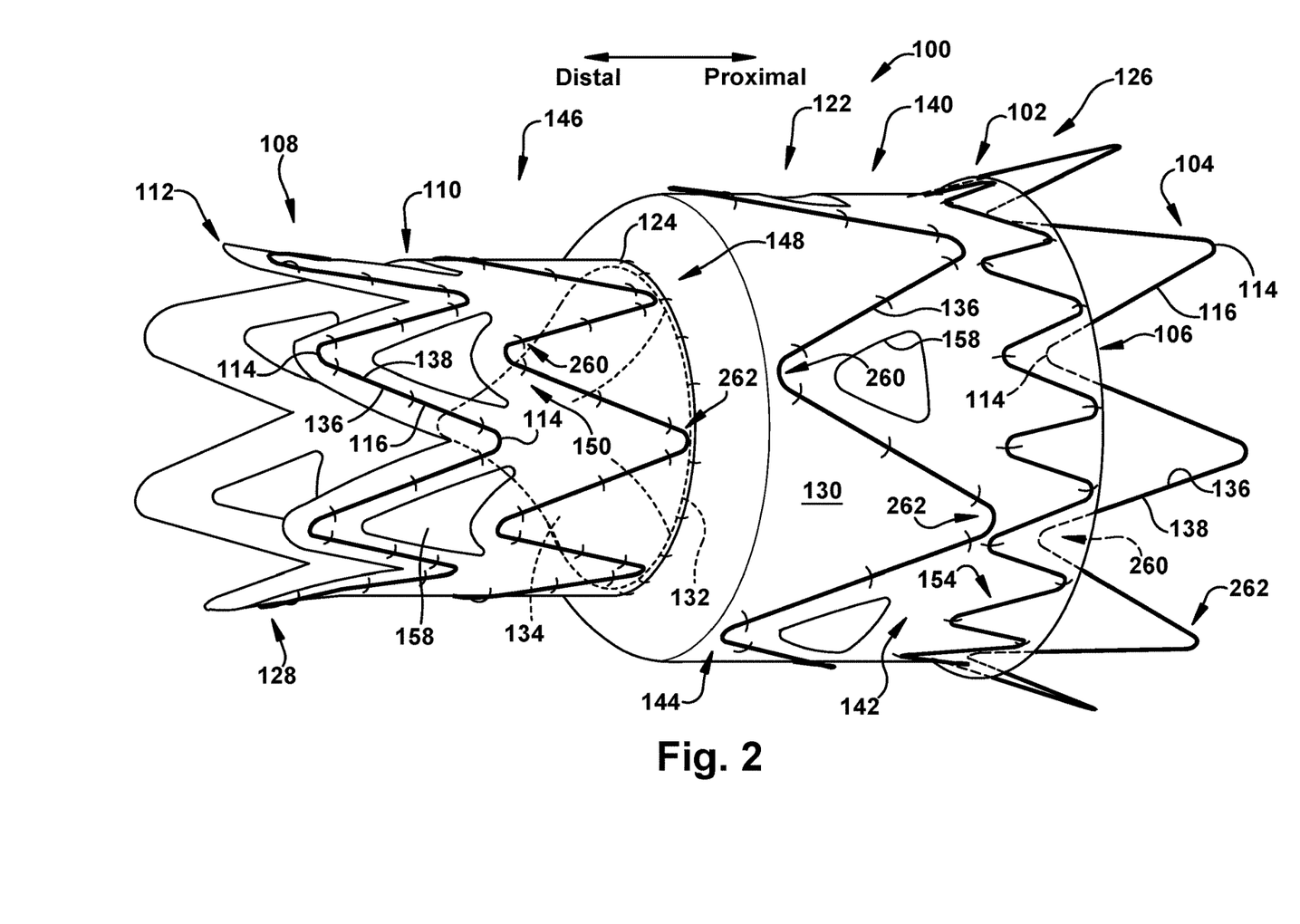
FIG. 2 is a side view of an aspect similar to that of FIG. 1.
Figure 3:
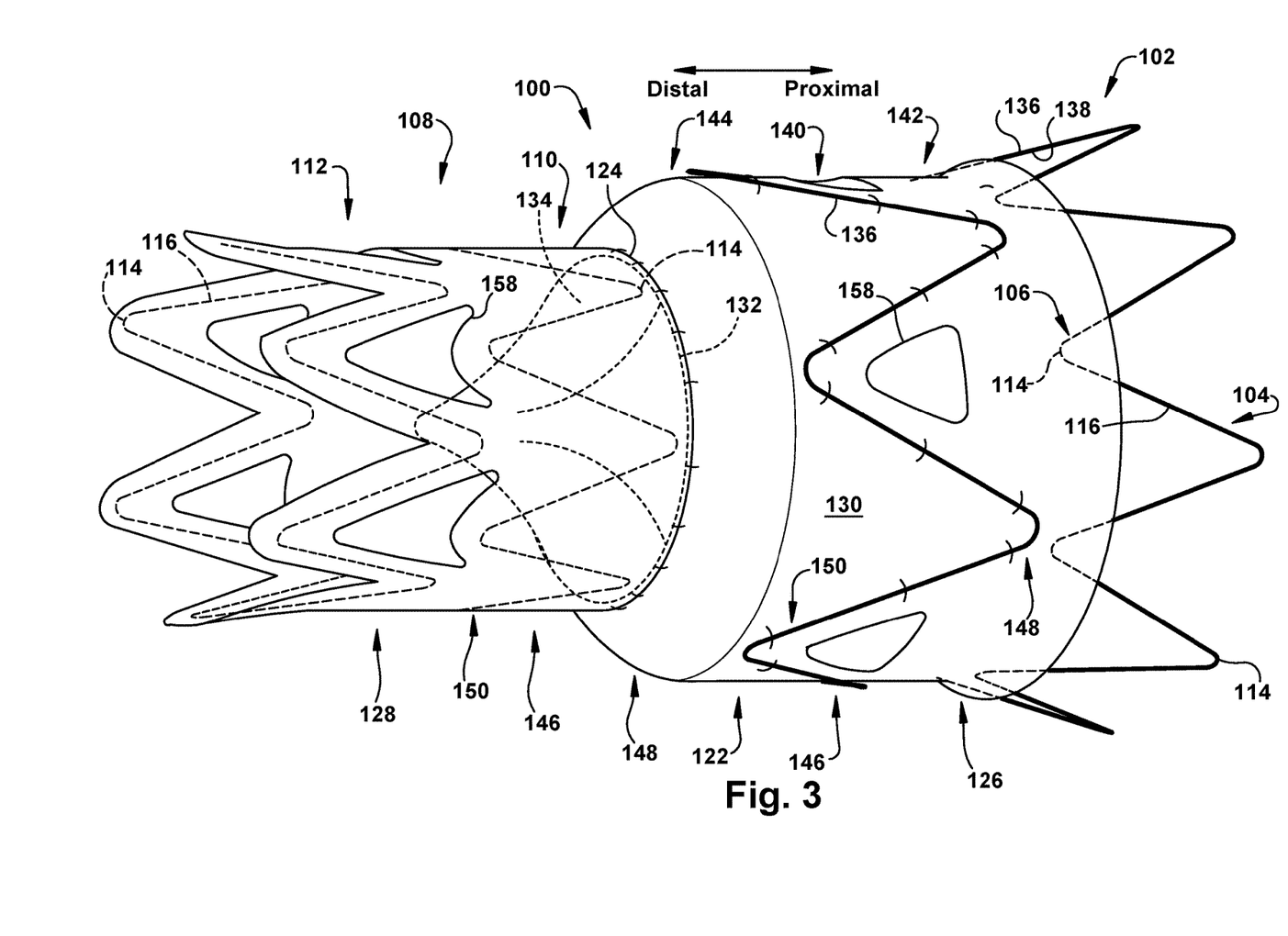
FIG. 3 is a partial side view of the aspect of FIG. 2.

As shown in FIG. 2, each of the first, second, third, and fourth support members 102, 108, 140, and 146 may include a plurality of distally-oriented peaks 260 and proximally-oriented valleys 262 (corresponding numbers omitted from other Figures for clarity). A plurality of graft apertures 158 may be configured to divide the graft section body 130 circumferentially (e.g., laterally) between the graft apertures 158 into a plurality of graft bridges 164 oriented in a substantially axial direction and extending between circumferentially aligned distally-oriented peaks 262 and proximally-oriented valleys 264 of axially adjacent ones of the first, second, third, and fourth support members 102, 108, 140, and 146.

Optionally, and as shown in at least FIG. 1, the proximal first support member end 104 may be axially spaced proximally from the proximal graft section end 126, such that a portion of the first support member 102 protrudes proximally beyond the graft section 122. Also optionally, and as shown in the Figures, the graft section 122 may be the only structure directly connecting the first, second, third, and fourth support members 102, 108, 140, and 146 together.

One use environment for the apparatus 100 is to repair the function of the diseased tricuspid valve 466, as shown in FIG. 4. To enable delivery and deployment of the apparatus 100, the apparatus 100 is radially collapsed and loaded into a sheath (not shown) over a catheter (not shown). After de-airing of the assembly, the apparatus 100 is delivered via a venotomy into the femoral vein and may be assisted with access through an internal jugular vein to establish through-and-through wire access. In the application of the apparatus 100 illustrated in FIG. 4, a first apparatus 100A is delivered to a desired location in the inferior vena cava (IVC) just below the right atrium (RA), potentially spanning across the hepatic veins 468 as shown (with certain graft apertures 158 aligned with those veins) but above the left renal vein, under fluoroscopic and/or transesophageal echocardiographic guidance.

Once the first apparatus 100A is advanced to the desired location, the sheath is retracted to allow the first and second support members 102A and 108A to expand radially outward into engagement with the heart wall structures as shown in FIG. 4 It should be noted that a balloon (not shown) may be used to assist with the expansion or stabilization of one or both of the support members 102A and 108A. As the support members 102A and/or 108A expand into the heart wall, the hooks 120, when present, on the beams 116 of the support members 102A and 108A may embed into the vessel wall to secure the apparatus 100A from migration in the IVC or right atrium.

Significantly, in the implanted condition shown in FIG. 4, the first support member 102A expands to the first diameter D1, which is the diameter of the IVC at that specific vascular location, and is able to independently expand and contract with the IVC in accordance with fluctuations in venous pressure or capacitance. Furthermore, the second support member 108A expands to the second diameter D2, which may be the diameter of an adjacent heart wall at that location, and is able to independently expand and contract with the heart wall structures in accordance with fluctuations in venous pressure or capacitance. In addition, the proximal graft section end 126B associated with the proximal first support member end 104A seals against the wall of the IVC to prevent any blood leakage around the apparatus 100A.

Further, the extra-cardiac location of the apparatus 100A may help reduce potentially detrimental effects of cardiac contraction and provides an anatomically favorable region for fixation and sealing. Finally, in the location shown in FIG. 4, the apparatus 100A may reduce or eliminate reversed systolic flow through the hepatic veins 468 and IVC.

Also shown in FIG. 4, a second apparatus 100B may also or instead be placed for repairing the function of the tricuspid valve 466 in the superior vena cava (SVC). The apparatus 100B is delivered to a desired location in the SVC just above the right atrial junction, but below the junction of the brachiocephalic and jugular veins, under fluoroscopic and/or transesophageal echocardiographic guidance. As with the first apparatus 100A above and the hepatic veins 468, the second apparatus 100B may span the azygous vein 470 as shown (with certain graft apertures 158 aligned with that vein). The apparatus 100B is then deployed in the same basic manner as described above with regard to placement in the IVC.

In the implanted condition of the second apparatus 100B shown in FIG. 4, the second support member 108B expands to the second diameter D2, which is the diameter of the chosen valve. Furthermore, the first support member 102B expands to the first diameter D1, which is the diameter of the SVC at that specific vascular location, and is able to independently expand and contract with the SVC in accordance with fluctuations in venous pressure or capacitance. In addition, the proximal graft section end 126B associated with the proximal first support member end 104B seals against the wall of the SVC to prevent any blood leakage around the second apparatus 100B.

Notwithstanding the flexibility of the diameters of the first and second support members 102 and 108 or the relative position of any apparatus 100 within the heart, the diameter of the prosthetic valve 132 may be predetermined by the size of the annulus 124 of the graft section 122 and may be, therefore, functionally independent of the diameters D1 and D2 of the first and second support members 102 and 108 (or the relative diameters of any other provided support members). This functional independence, when present, of the diameter of the prosthetic valve 132 suspended within the graft section 122 helps to prevent antegrade and retrograde blood leaks around the prosthetic valve 132 and helps lead to proper valvular function. The prosthetic valve 132 can be provided to the apparatus 100 in any desired manner, including being sewn in by hand before or after the apparatus 100 is collapsed and delivered to the desired installation site, or delivered percutaneously, such as via a staged procedure with a transcatheter aortic valve replacement ("TAVR") device.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:

1. An apparatus for repairing the function of a diseased valve, the apparatus comprising:
   a tubular first support member expandable to a first average diameter and having oppositely disposed proximal and distal first support member ends;
   a tubular second support member spaced axially apart from the first support member and expandable to a second average diameter that is smaller than the first average diameter, the second support member having oppositely disposed proximal and distal second support member ends; and a tubular graft section interconnecting the first and second support members and defining an annulus axially spaced from both the first and second support members, the tubular graft section having oppositely disposed proximal and distal graft section ends axially spaced apart by a graft section body, the proximal graft section end being connected directly to the distal first support member end and the distal graft section end being connected directly to the proximal second support member end, a diameter of the tubular graft section at the proximal graft section end being larger than a diameter of the tubular graft section at the distal graft section end, the graft section overlapping and being secured to an outer surface of one of the first and second support members and the graft section underlying and being secured to an inner surface of the other of the first and second support members.

2. The apparatus of claim 1, including a prosthetic valve secured within the annulus of the graft section, the prosthetic valve having at least two valve leaflets that are coaptable to permit the unidirectional flow of blood; wherein the first and second support members are interconnected only by the graft section, and the prosthetic valve is directly secured only to the graft section.

3. The apparatus of claim 1, including a tubular third support member spaced axially apart from, and distal to, the first support member and expandable to a third average diameter that is substantially similar to the first average diameter, the third support member having oppositely disposed proximal and distal third support member ends, the third support member being connected directly to the graft section body.

4. The apparatus of claim 3, wherein the graft section underlies and is secured to an inner surface of the third support member.

5. The apparatus of claim 3, wherein the graft section body includes at least one graft aperture penetrating therethrough, the graft aperture being located axially between circumferentially corresponding portions of axially adjacent ones of the first, second, and third support members.

6. The apparatus of claim 5, wherein each of the first, second, and third support members includes a plurality of distally-oriented peaks and proximally-oriented valleys, and wherein a plurality of graft apertures are configured to divide the graft section body circumferentially between the graft apertures into a plurality of graft bridges oriented in a substantially axial direction and extending between circumferentially aligned distally-oriented peaks and proximally-oriented valleys of axially adjacent ones of the first, second, and third support members.

7. The apparatus of claim 1, wherein the proximal first support member end is axially spaced proximally from the proximal graft section end.

8. The apparatus of claim 1, including a tubular fourth support member spaced axially apart from, and proximal to, the second support member and expandable to a fourth average diameter that is substantially similar to the second average diameter, the fourth support member having oppositely disposed proximal and distal fourth support member ends, the fourth support member being connected directly to the graft section body.

9. The apparatus of claim 8, wherein the graft section underlies and is secured to an inner surface of the fourth support member.

10. The apparatus of claim 1, wherein the graft section is the only structure directly connecting the first and second support members together.

11. The apparatus of claim 8, wherein the graft section body includes at least one graft aperture penetrating therethrough, the graft aperture being located axially between circumferentially corresponding portions of axially adjacent ones of the first, second, third, and fourth support members.

12. The apparatus of claim 11, wherein each of the first, second, third, and fourth support members includes a plurality of distally-oriented peaks and proximally-oriented valleys, and wherein a plurality of graft apertures are configured to divide the graft section body circumferentially between the graft apertures into a plurality of graft bridges oriented in a substantially axial direction and extending between circumferentially aligned distally-oriented peaks and proximally-oriented valleys of axially adjacent ones of the first, second, third, and fourth support members.

* * * * *